United States Patent [19]

Carter

[11] Patent Number: 5,683,986
[45] Date of Patent: Nov. 4, 1997

[54] ELABORATION OF HOST DEFENSE MEDIATORS INTO BIOLOGICAL FLUIDS BY SYSTEMIC DSRNA TREATMENT

[75] Inventor: William A. Carter, Birchrunville, Pa.

[73] Assignee: Hemispherx Biopharma Inc., Del.

[21] Appl. No.: 384,396

[22] Filed: Feb. 3, 1995

Related U.S. Application Data

[63] Continuation of Ser. No. 131,411, Oct. 4, 1993, abandoned, which is a continuation of Ser. No. 993,901, Dec. 18, 1992, abandoned, which is a continuation of Ser. No. 778,751, Oct. 18, 1991, abandoned, which is a continuation of Ser. No. 637,947, Jan. 8, 1991, abandoned, which is a continuation of Ser. No. 443,833, Dec. 1, 1989, abandoned, which is a continuation of Ser. No. 227,950, Aug. 3, 1988, abandoned, which is a continuation-in-part of Ser. No. 84,227, Aug. 12, 1987, abandoned.

[51] Int. Cl.$^6$ .................... A61K 48/00; A61K 31/785; A61K 31/80; C07H 21/02
[52] U.S. Cl. .................... 514/44; 536/23.1; 536/25.1; 536/25.5; 435/375; 424/280.1
[58] Field of Search .................... 514/44; 536/23.1, 536/25.5, 25.1; 435/375; 424/280.1

[56] References Cited

U.S. PATENT DOCUMENTS

| | | | |
|---|---|---|---|
| 3,931,397 | 1/1976 | Hamden | 424/85 |
| 4,140,761 | 2/1979 | Gerin et al. | 424/85.4 |
| 4,795,744 | 1/1989 | Carter | 514/44 |
| 4,820,696 | 4/1989 | Carter | 514/44 |

FOREIGN PATENT DOCUMENTS

| | | |
|---|---|---|
| 0113162 | 9/1983 | European Pat. Off. |
| 0213921 | 9/1983 | European Pat. Off. |

OTHER PUBLICATIONS

R. Suhodolnik et al., Clinical Infecious Diseases vol. 18, Suppl. 1:S 96–S 104 1994.

D. Strayer et al., J. of Chronic Fatigue Syndrome vol. 1(1):35–53 1995.

D. Drutz et al., in Basic & Clinical Immunol., Ed. by D. Stites, J. Sroho, et al., Lange Medical Publications, Los Altos, CA ('84) pp. 197–222.

*Nature*, vol. 242, No. 5399, Apr. 20, 1987, pp. 525–526, M. Koltai et al "Inhibition of the Acute Inflammatory Response by Interferon Inhibitors".

*The Lancet*, Jun. 6, 1987, pp. 1286–1292, Carter et al. "Clinical Immunological and Virological Effects of Ampligen . . . ".

*Journal of Biological Response Modifiers*, vol. 4, 1985, pp. 669–675 I. Brodsky et al "Clinical Studies with Ampligen . . . ".

*Journal of Biological Response Modifiers*, vol. 4, 1985, pp. 495–502 Carter et al, "Preclinical Studies with Ampligen . . . ".

*Springer Semin. Immunopathol.*, vol. 2, 1979, pp. 149–168, Johnson "Modulation of the Immune System by Synthetic Polynucleotides".

*Handbook of experimental Pharmacology*, vol. 71, pp. 536–555, Came et al "Therapeutic Applications of Double-Stranded RNAs".

*Mol. Pharmacol.*, vol. 12, No. 2, 1976, pp. 299–312, P. TS'O et al "An Integrated and Comparative Study of the Antiviral Effects and . . . ".

*Primary Examiner*—Charles C. P. Rories
*Attorney, Agent, or Firm*—Nixon & Vanderhye

[57] ABSTRACT

Parenterally administered systemic dsRNAs release host mediators into various compartmentalized biological fluids to combat various microorganisms, particularly viruses, thereby reducing the infectivity and spread of various organisms including those associated with various diseases such as those caused by venereal warts, herpes and HIV.

2 Claims, 3 Drawing Sheets

FIG. 2

FIG. 3 under the sumber 5,683,986

ELABORATION OF HOST DEFENSE MEDIATORS INTO BIOLOGICAL FLUIDS BY SYSTEMIC DSRNA TREATMENT

This is a Rule 62 File Wrapper Continuation of application Ser. No. 08/131,411, filed Oct. 4, 1993, which is a continuation of Ser. No. 07/993,901 filed Dec. 18, 1992 which is a continuation of Ser. No. 07/778,751, filed Oct. 18, 1991 which is a continuation of Ser. No. 07/637,947 filed Jan. 8, 1991 which is a continuation of Ser. No. 07/443,833 filed Dec. 1, 1989 which is a continuation of Ser. No. 07/227,950 filed Aug. 3, 1988 which is a continuation-in-part of Ser. No. 07/084,227 filed Aug. 12, 1987, all of the above-issued patent applications being now abandoned.

Biological fluids including tears, vaginal secretions, and male ejaculates (sperm enriched) can contain various microorganisms (fungi, bacteria, viruses), capable of causing and spreading various dreaded diseases. Topical or direct antimicrobial treatments (foams, sprays, etc.) are often used despite their limited value because of the sequestered nature of the microorganism(s), making them relatively non-accessible to the treatments. Topical applications can also be limited by virtue of the local irritation they cause as well as their heightened potential for causing an allergic reaction. I describe herein parenteral routes of administration of administering dsRNAs which result in the unexpected release of host defense mediators into various biological fluids including those regularly exchanged during coitus. Accordingly, I have described a new technique for reducing the infectivity and spread of various organisms, including those associated with various diseases including those caused by venereal warts, herpes and human immunodeficiency virus, etc.

BACKGROUND OF THE INVENTION

Newer products which may play crucial roles in fighting off infections and cancers are the so-called immuno-modulators, such as interferons (IFN), interleukins (IL) and tumor necrosis factor (TNF). They are proteinaceous drugs which can increase or trigger the body's natural disease-fighting efforts. However, such protein-containing products cannot generally be given in liquid or tablet form because the stomach destroys there proteins before they can be absorbed into the blood stream. Moreover, their parenteral (IV, IM or subcutaneous) administration can also produce troublesome side effects, especially with higher drug concentrations or over very lengthy treatment periods. Accordingly, researchers have tried to develop such drugs in topically active preparations for use on the skin, eyes, and especially to combat various venereal diseases. For example, Rapp and Wrzos (*Antimicrobial Agents and Chemotherapy*, Vol. 28, pg. 449, 1985) described a contraceptive foam or cream in which an antiviral agent (IFN) was combined with a nonionic surfactant detergent, a primary purpose of which was to protect one (or both) partners during coitus from herpes virus spread. The relative effectiveness of such topically-applied preparations, etc., is not yet elucidated; however, previous use of topically applied antiviral preparations has met with limited success. Limitations of such approaches include the sequestered nature (not accessible to the preparation) or some viral particles as well as the reduced local immune capacity of the infected region of the body making any durable therapeutic response unlikely.

Tissues infected with viruses susceptible to IFN, such as viral (herpes simplex) infections of the skin, eye and mucous membrane, are treated with topical compositions of the interferon inducers dsRNAs, notably poly I·C, in a sustained release formulation as described in U.S. Pat. No. 4,283,393 (Field et al). The patent literature also describes topically-applied antiviral agents, such as nonionic surfactants as inactivating agents for herpes simplex, as in U.S. Pat. No. 4,020,183 (Asculai et al) alone or in combination with interferon, as in U.S. Pat. No. 4,507,281 (Asculai et al).

I have overcome these inherent limitations of prior procedures and materials by a surprising and novel group of observations in which I show that parenteral administration of dsRNA causes release of bioactive dsRNA fragments which readily cross the blood-brain barrier and enter the compartmentalized fluids including saliva, tears, serous fluids, serous exudates and the like. These disease fighting mediators readily enter into various biological fluids—even in the absence of detectable intact dsRNA within the fluids themselves.

The term "compartmentalized body fluid" as used herein refers to a localized body fluid from outside the systemic blood circulation. These compartmentalized body fluids include fluids on serosal surfaces, mucousal surfaces, the synovial lining, urethral surfaces, cervical or lining, the cerebrospinal fluid and in the occular fluid compartment.

I specifically show the elaborations of mediators which are capable of directly attacking viruses and simultaneously arming the local immune system, as within the genito-urinary system. By practicing the invention, I illustrate dramatically how the ejaculate of male can be essentially reduced or perhaps eradicated of potentially high levels of viruses (including HIV, the herpes viruses and cytomegalovirus) which otherwise could cause both himself and his sexual partners various dreaded diseases. The invention is immediately relevant also to production of disease-fighting mediators within exudates or transudates (arthritic joints) and the cerebrospinal fluids. Thus, the invention is directly pertinent to such diverse diseases as various arthritis and central nervous system diseases.

In European Patent Application published as 0 213 921 on Mar. 11, 1987, entitled "Modulation of Virus-Related Events by Double-Stranded RNAs", the inventor describes the inhibition of HIV in human cell culture by dsRNAs, specifically using Ampligen® as a prototype dsRNA.

DESCRIPTION OF THE INVENTION

Described are procedures for activating the natural antiviral pathways and arming the immune system of an individual prior to exposure to, to prevent, or after contracting, to treat, a disease, the object of the activation to induce the patient's body to release disease-fighting mediators into various biological fluids, including biological fluids within localized body compartments, as explained below. Parenteral administration of dsRNA, preferably a mismatched dsRNA, as explained in more detail below, causes the release of bioactive dsRNA fragments, sometimes referred to herein as disease fighting mediators, into these biological fluids, even in the absence of detectable intact dsRNAs within the fluids themselves. These bioactive dsRNA fragments readily cross the blood-brain barrier and other body compartments separated from the general blood circulation by tissue and locate in the fluid(s) desired.

Diagnostic test procedures for measuring inactive host/patient defense mediators in biological fluids and, if insufficient, administering a dsRNA in an amount and for a period of time sufficient to reduce the amount of pathogenic agent or agents and/or reduce the disease processes and restore the requisite dsRNA for bioactive fragments thereof to thereby improve the biochemical parameters of the defense mediators in the fluid under examination are also described.

The disease diagnosed and/or treated by the process of this invention may be viral in nature, e.g., a virus of the herpes family including cytomegalovirus, a virus of the retrovirus family including HIV, an inflammatory disease such as arthritic disorders, diseases of sensitive bacterial species or diseases of fungal or protozoal origin.

There is a wide range of pathogenic agents potentially sequestered in biological fluids outside the blood stream. These compartmentalized biological fluids (excluding blood) are usually inaccessible to drug macromolecules (proteins, nucleic acids, etc.) administered systemically. As used herein and understood in the medical arts, administered parenterally means put directly into the blood, via an IV infusion, etc., or put into a compartment which is readily accessible to blood stream such as a drug macromolecule delivered via an initial intramuscular or subcutaneous delivery (injection). Also, such high molecular weight macromolecules could be delivered orally if properly encapsulated, enteric coated or protected, or otherwise made relatively impregnable to destructive forces such as pH and enzymes encountered in the upper gastro-intestinal tract. All such delivery modes would yield more or less detectable levels or macromolecules in the blood stream eventually, but not necessarily in other biological fluids (serous)—at least certainly not in a highly bioactive form or configuration.

The inability to reach such distal compartmentalized fluids is due largely to the physical barriers (membranes, cells, etc.) which serve to protect various body compartments (G-U tract, joints, oral cavity, CNS, etc.) from the ready crossing of pathogenic agents from one compartment of the body to another (i.e., pathogenic spread). Thus, while such physical barriers have an obvious value to man in terms of localizing diseases and reducing spread of microorganisms including viruses, such barriers serve as a significant impediment to the facile distribution of such disease fighting substances as immunomodulators which tend to be (a) macromolecular (though not always), and (b) not readily able to penetrate such "barriers" including cell/membrane gradients. Accordingly, various researchers have explored ways to deliver such immunomodulators/antivirals/anticancer compounds directly into localized body compartments via physiologically-compatible carriers as tampons, condoms and the like. To date, such approaches have met with only limited success.

A surprising breadth of pathogenic microorganisms are either sequestered in such serous compartments as a portal of initial entry into the human body. A venereal (coitus-related) mode of transmission is obviously especially alarming with respect to chlamydia (associated with pelvic inflammatory disease and infertility) and various viruses.

For example, genital and oral herpes, cytomegalovirus, genital warts and retroviruses (especially HIV) are being spread with alarming rates and there is no present evidence to indicate that approaches such as interferon-based topical preparations or interferon-inducer topical preparations, etc., will be definitive treatments or prophylactic approaches.

An objective of this invention, then, is to devise a mode of treatment which efficiently produces disease-fighting mediators in a variety of serous fluids largely throughout the patient's body; the treatment may be used alone or in conjunction with topical treatments. An additional value of my invention is that it can be practiced in tandem with traditional approaches such as interferon-impregnated tampons, etc., if further degrees of topical protection to interferon-sensitive diseases are desired.

I have observed a previously undetected biochemical anomaly in which a key enzyme (RNase L) associated with the body defense mechanisms against both cancer and viral diseases is operating in an accelerated and apparently uncontrolled manner. These and other observations are described in my copending application U.S. Ser. No. 07/074,649 filed Jul. 17, 1987, and entitled "Double-Stranded RNA Correction of Aberrant Metabolic Pathways Associated With Uncontrolled Tumor Cell and Virus Growth Cycles", the disclosure of which is hereby incorporated by reference. In separate experiments, I compared the relative abilities of these two different cells with abnormal RNase L and those with normal amounts of RNase L) to withstand viral challenge. I observed that the titers (yield) of progeny retroviruses were significantly higher in those cells with the abnormal RNase L activity which generated to NCP so rapidly.

Double-stranded RNAs, especially mismatched dsRNAs, restore normalcy of RNase L kinetics and degradation products as reported in my U.S. patent application Ser. No. 07/074,649, noted above. Further, the rate of restoration of normalcy by double-stranded RNA can be accelerated by prior exposure to lymphokines.

Double stranded RNAs (dsRNAs) are double stranded synthetic polynucleotide complexes. By "mismatched dsRNAs" are meant those in which hydrogen bonding (base stacking) between the counterpart strands is relatively intact. Mismatching is an interruption of the normal geometry of the RNA double helix by in-pouching (or out-pouching) of the strands which represent points of vulnerability of the dsRNA to digestion by ribonucleases. The term "mismatched dsRNA" should be understood accordingly.

The dsRNA may be a complex of polyinosinate and a polycytidylate containing a proportion of uracil bases or guanidine bases, e.g., from 1 in 5 to 1 in 30 such bases (poly I·($C_{4-29}$x>U or G).

The dsRNA may be of the general formula $rI_n\cdot(C_{11-14},U)_n$ or $rI_n\cdot(C_{12}U)_n$. The value of n is from 4 to 29. Other suitable examples of dsRNA are discussed below.

The mismatched dsRNAs preferred for use in the present invention are based on copolynucleotides selected from poly ($C_n$,G) in which n is an integer having a value of from 4 to 29, and are mismatched analogs of complexes of polyriboinosinic and polyribocytydilic acids, formed by modifying $rI_n\cdot rC_n$ to incorporate unpaired bases (uracil or guanidine) along the polyribocytidylate ($rC_n$) strand. Alternatively, the dsRNA may be derived from poly (I)·poly (C) dsRNA by modifying the ribosyl backbone of polyriboinosinic acid ($rI_n$) e.g., by including 2'-O-methyl ribosyl residues. These mismatched analogs of $rI_n\cdot rC_n$, preferred ones of which are of the general formula $rI_n\cdot r(C_{11-14},U)_n$ and $rI_n\cdot r(C_{29},G)_n$, are described by Carter and Ts'o in U.S. Pat. Nos. 4,130,641 and 4,024,222 the disclosures of which are hereby incorporated by reference. The dsRNAs described therein generally are suitable for use according to the present invention.

In the preferred mismatched dsRNA, $rI_n \cdot (C_{12},U)_n$, a region consisting of an uninterrupted stretch of 6 to 12 base pairs, i.e., one-half to one full turn of an RNA helix, serves both as a biotrigger causing release of lymphokines as an obligate intracellular co-factor for enzymes comprising the natural antiviral pathways. The mismatched regions consisting of uracil residues is periodically inserted in the polypyrimidine strand to accelerate dsRNA hydrolysis and thus prevent toxicity.

Other examples of mismatched dsRNA for use in the invention include:

poly (I)·poly ($C_4$,U)

poly (I)·poly ($C_7$,U)

poly (I)·poly ($C_{13}$,U)

poly (I)·poly ($C_{22}$,U)

poly (I)·poly ($C_{20}$,G)

poly (I)·poly ($C_{29}$,G)

As discussed herein, lymphokines will be understood to include the interferons, preferably interferon alpha, the interleukins, specifically interleukin-2 (IL-2) and recombinant interleukin-2 (rIL-2), and tumor necrosis factor (TNF). Also included are lymphokine activated killer (LAK) cells formed in animals in response to exposure to a lymphokine.

When interferon (alpha) is used as the lymphokine, an amount of from 0.01 to 100,000 IRU per milliliter of the patient's body fluid is provided. When IL-2, preferably rIL-2, is the lymphokine, the amount administered lies within a range of about $10^2$ IL-2 units per kg of the patient's body weight up to a value approaching unacceptable levels of toxicity in that patient, which may be as high as $10^6$ IL-2 units. However, most effective, toxic-reaction manageable values are in the range of from about $10^3$ to about $10^4$ IL-2 per kg of body weight.

The usual amounts of dsRNA administered provide a level of from 0.1 to 1,000 micrograms dsRNA per milliliter of the patient's body fluid. The term body fluid is intended to refer to that solution of serum, salts, vitamins, etc., which circulates within the organism and bathes the tissues. The patient's body fluid volume is determined in available medical tables which interrelate the weight of the recipient to his or her body fluid volume, which is the total of the patient's body fluid volume and the body fluid volume available for equilibration with the necessary quantity of the dsRNA. As an example, a 60 or 70 kilogram patient will have a body fluid volume of approximately 5 to 6 liters. When both agents (a dsRNA and a lymphokine) are administered they may be administered as a mixture, administered separately but simultaneously, or sequentially.

Administration of a dsRNA and a lymphokine "in combination" includes presentations in which both agents are administered together as a therapeutic mixture, and also procedures in which the two agents are administered separately but simultaneously, e.g., as through separate intravenous lines into the same individual. Administration "in combination" further includes the separate administration of one of the drugs in which one of the drugs is given first followed shortly by the second.

EXAMPLE 1

I administered mismatched dsRNAs [AMPLIGEN® (HEM Research, Inc., Rockville, Md.) a mismatched dsRNA of the formula $rI_n \cdot r(C_{12},U)_n$)] in amounts between 20 and 1000 grams weekly (IV) to groups of individuals weighing between 40 and 70 kilograms and evaluated their serous fluids, especially vaginal fluids and male ejaculate, for the possible presence of dsRNA-induced host defense mediators. In companion clinical testing, I studied similar parameters in individuals infused with either interferons or interleukins to determine the specificity, if any, of the processes. Under light microscopy, the fluid isolated from the patients treated contained a variety of cells including mononuclear cells, squamous epithelia (female genitalia samples) and spermatozoa (male ejaculate) as well as rather amorphous cell "debris".

A summary of the observations in treating three such patients with the dsRNA for various periods of time is given in the following Table:

TABLE 1

Effect of Systemic dsRNA Treatment on Level of Recoverable Virus in Compartmentalized Biological Fluid(s)

| Patient | Time | Exogeneous dsRNA (Amt. Received in grams) | |
|---|---|---|---|
| | | | Virus Load by Coculture |
| 1. Patient A (male with HTLV-III infection) | pretreatment 4 weeks 30 weeks | 0 1.6 12 | 0.6, 0.8, 0.5 0.3, 0.25, 0.25 0.2, 0.15, 0.15 |
| 2. Patient B (male with HTLV-III infection) | pretreatment 8 weeks 40 weeks | 0 2.8 10.0 | 1.5, 1.2, 1.2 0.6, 0.5, 0.7 0.15, 0.10, 0.18 |
| | | | Virus Titer (PFU) |
| 3. Patient C (female with chronic herpes simplex [HS] type 2 infection) | pretreatment 8 weeks 36 weeks | 0 2.6 10.8 | $1 \times 10^4, 2 \times 10^4, 2 \times 10^4$ $2 \times 10^3, 5 \times 10^2, 1 \times 10^3$ $<1 \times 10^2, <1 \times 10^2, <1 \times 10^2$ |

Patients A and B had high titers of recoverable HIV-III from ejaculate when 2.0–4.0 cc of ejaculate was measured by co-culture utilizing a technique I recently reported for peripheral blood mononuclear cells (Carter et al, Lancet, Vol. 1, Jun. 6, 1987, pg. 1287). Briefly, I exposed blood mononuclear cells from a normal donor which had been stimulated with PHA for 2–4 days and continued culture for 28 days and then measured extracellular virus by an enzyme-linked immunosorbent assay (ELISA). The co-culture titer was defined as the average optical density (OD at 490 mm) of the ELISA assay after subtraction of a negative control value (less than 0.1). Patient C had chronic HS expression in vaginal secretions associated with perianal vesicle formation. Herpes simplex was cultured by the method of Rapp utilizing confluent HEL cells propagated in 35 mm plates (Rapp et al *Antimicrob. Agents & Chemoth.*, Vol. 28, p. 449, 1985).

Figure 1:
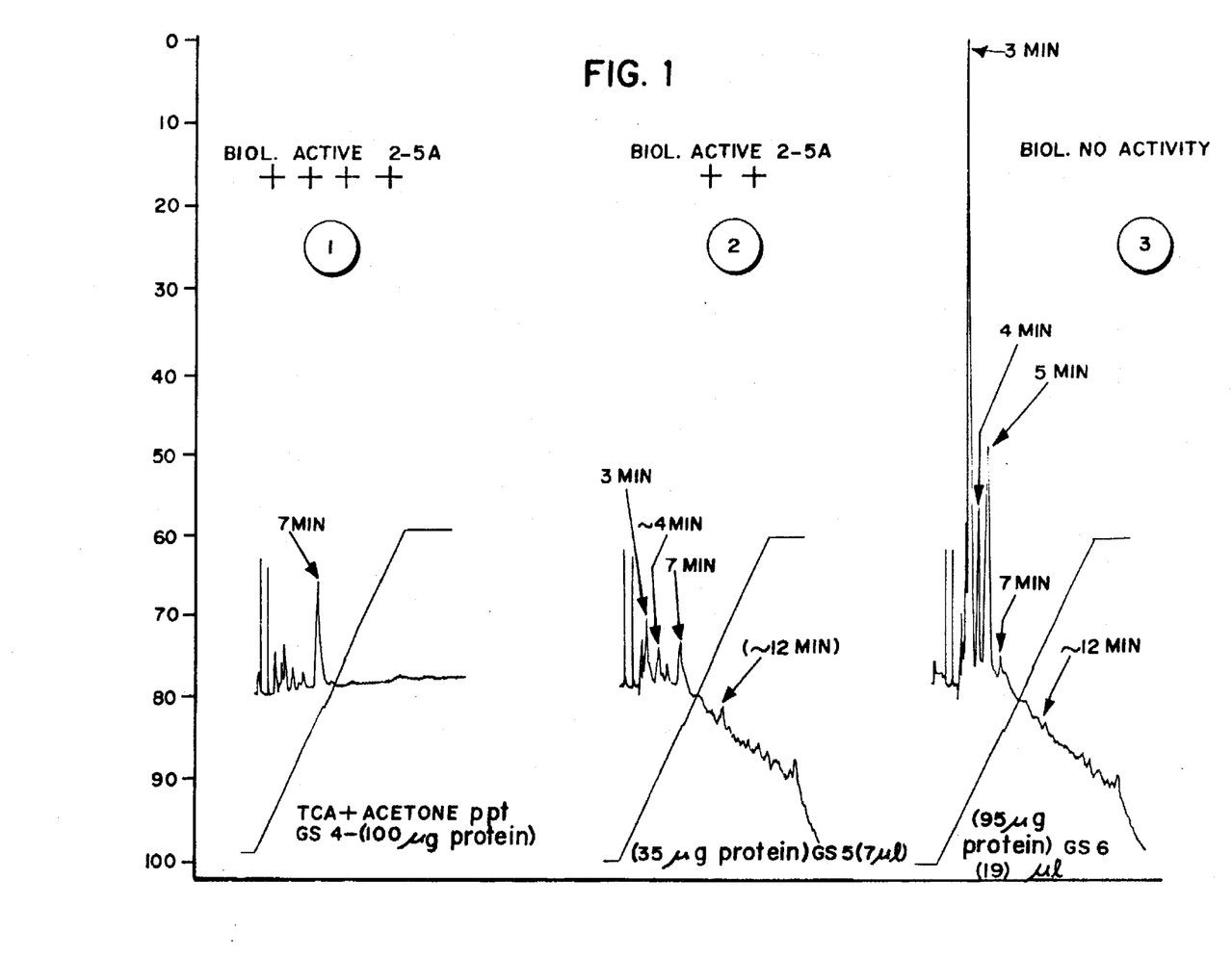
FIG. 1 is a three-part high-pressure chromatography (HPLC) graph measuring a patient's biological fluid for various components of the natural (2'-5' oligo A/RNase L) antiviral pathway before and after dsRNA administration for patient A of Example 1.
Figure 2:
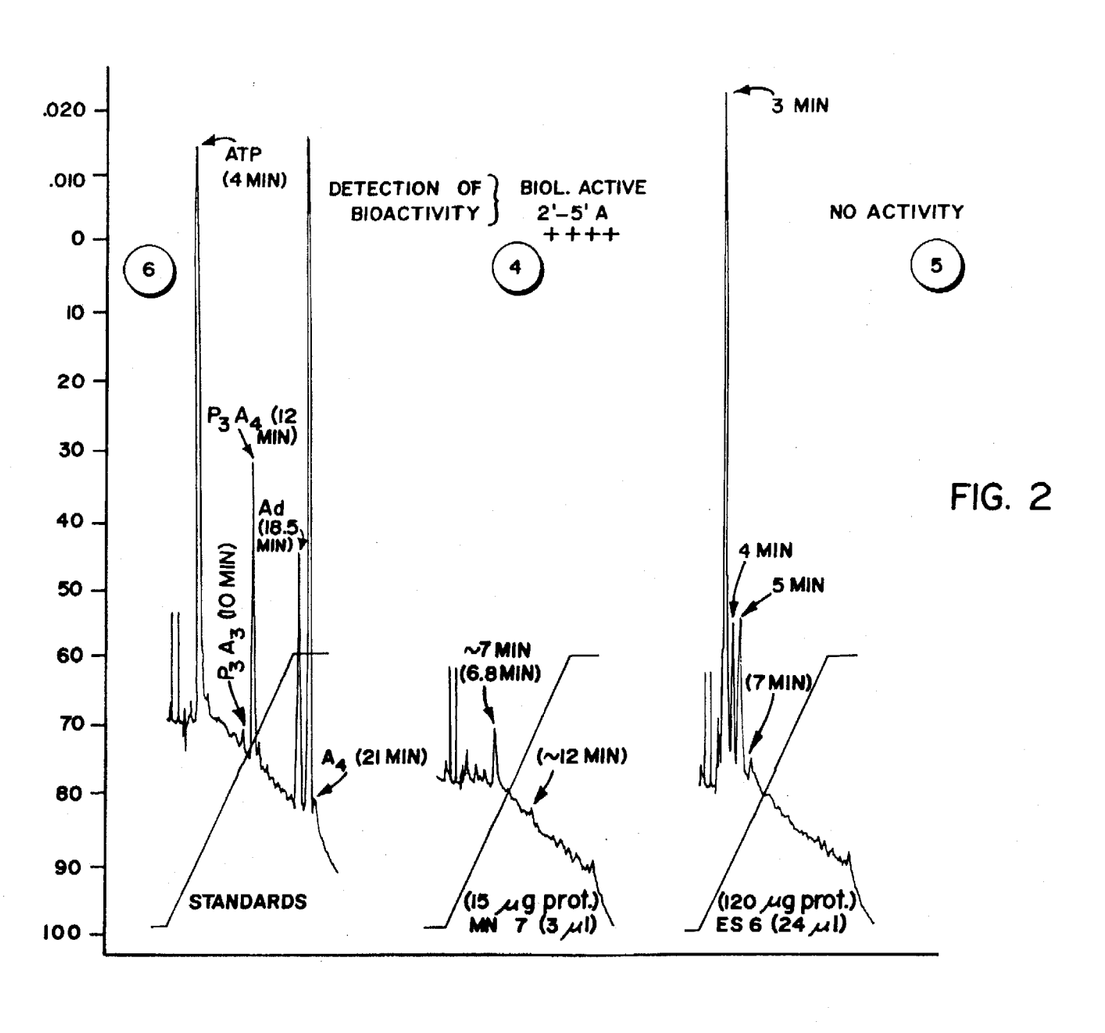
FIG. 2 is a three-part graph showing a standardized calibration (lane 6) and the results of HPLC analysis (lanes 4 and 5) from patient B of Example 1.

Attached FIGS. 1 and 2 report the result of HPLC evaluation of patient fluid samples before and after the systemic administration of the dsRNA $rI_n \cdot r(C_{12},U)_n$ alone and in combination with lymphokines. In FIG. 1, all samples were prepared by TCA and acetone precipitation as were the samples in columns 4 and 5 of FIG. 2. FIG. 2, column 6 was used to establish a standardized calibration tracing, as explained below. The figures are arranged as follows: FIG. 1, column 3 is patient A prior to treatment; column 2 after 4 weeks of treatment, and column 1 following 12 weeks of treatment; FIG. 2, column 5 is patient B before treatment and column 4 during treatment, column 6 is a standardization curve. FIGS. 1 and 2 are to be compared with Table 1, above.

Evaluation of patient samples with high pressure liquid chromatography (HPLC) after systemic administration of dsRNA shows enhancement of host defense mediators. Patients' vaginal (no. 3) and ejaculate (no. 1 and 2) fluids were evaluated with respect to various components of the natural (2'-5' oligo A/RNase L) antiviral pathway as I recently described for peripheral blood mononuclear cells (Carter et al, *Lancet*, cited above; also see Kariko et al, *Biochem. Biophys. Res. Comm.*, Vol. 128, pg. 695, 1985 and Suhadolnik et al, *Biochemistry*, Vol. 22, pg. 4153, 1983). The results are shown in graphically in FIGS. 1A, 1B, and 1C. I specifically found barely detectable activity of all system components before dsRNA administration. However, during systemic administration of dsRNA, I observed a specific enrichment in mediators in these serous fluids, as shown in FIGS. 1 and 2, which kinetically was coupled with reduction in viral expression in these same sites (Table 1) and in the complete absence of detectable macromolecular dsRNA. These values were measured by quick blotting and liquid scintillation spectrophotometry which I reported earlier (Brodsky et al *J. Biol. Response Modifiers*, Vol. 4, pg. 669, 1985).

To evaluate the specificity of the process, I also studied similar individuals (or animals) treated with high doses (<10 mil IRU (d)) of various interferons and interleukins, but failed to show any enhancement in disease fighting mediators in these compartmentalized fluids. However, when I combined systemically injected lymphokines with mismatched dsRNAs, the rate of detection of mediators in these compartmentalized fluids was noticeably accelerated. HPLC combined with radiobinding, radioimmune and rRNA cleavage assays confirmed the specific elaboration of novel 2'-5' oligoadenylate as a result of the dsRNA applied elsewhere in the body and in sufficient quantities to cause disease protection, the latter as clearly indicated by results of Table 1.

HPLC identification (see Lee and Suhadolnik, *Biochemistry*, Vol. 24, pg. 551, 1985) was carried out after sample preparation by TCA and acetone precipitation. A Waters $C_{18}$ micron Bondapak analytic column was used by developing gradients of methanol and water in an ammonium phosphate (50 mm) buffer, pH 7.0. HPLC run designated #6 (FIG. 2) shows a standard calibration with authentic $p_3A_3$ and $p_3A_4$ which had been synthesized enzymatically (Layley et al *Europ. J. Biochem.*, Vol. 143, Pg. 165, 1984 and references cited therein). The critical isolates are the HPLC peaks which appear either between 6.8 and 7.0 minutes or at approximately 12 minutes in this particular HPLC configuration because these peaks are indicative of the most bioactive mediators, namely those corresponding to authentic $p_3A_3$ and $p_3A_4$ which are, respectively, the trimer and tetramer of 2'-5' linked oligoadenylate mediators. Note that patient A of Table 1 [whose seminal ejaculate is analyzed pretreatment (column 3, FIG. 1) and post treatment (column 2 at 4 weeks and column 1 after 12 weeks)] shows a progressive increase in both bioactive 2'-5' A levels utilizing the standard RNase L cleavage assay and incremental levels of structurally authentic 2'-5 A molecules as determined by HPLC. Results similar to patient A were seen with patient B (results not shown). FIG. 2 shows results obtained with the vaginal secretions of patient C before (column designated 5) and during (column designated 4, FIG. 2) systemic dsRNA therapy. Note in patient C, by comparing Table 1 with FIG. 2, that the level of infections herpes virus fell dramatically as the level of mediators, measured both as bioactivity and authentic chemical structures, increased.

While not wishing to be bound by any particular theory or mode of operation, the mechanism by which I have achieved these effects in localized bodily compartments appears to involve, at least in part, a signal transductive process whereby dsRNA acts on cells surrounding or near blood vessel walls and this process causes a wave-like process triggering mediator formation within the localized compartment itself.

EXAMPLE 2

The inventor has determined that the unique structure of mismatched dsRNA is a most favorable modus operandi for practice of the subject invention. This is due to the fact that mismatching of dsRNA results in fragile regions within the otherwise relatively stable dsRNA complex: as a result, small bioactive fragments of dsRNA, being more mobile, can gain access to specialized bodily compartments in which they produce a localized, highly specific, immunomodulatory and antiviral effect. Gaining access to the otherwise sequestered compartment is not a property of most exogenously applied dsRNAs in my experience.

Among other experiments used to demonstrate this phenomena, I simulated in vivo conditions of biodegradation by exposing aliquots of perfectly base-paired dsRNA (poly I·poly C) and compared results with aliquots of mismatched dsRNA (poly I·poly $C_{12}$,U) to $S_1$ nuclease (a degradative enzyme for dsRNA). The profiles of the two degradation curves were completely different and, I believe, this difference lays at the base of the vastly different therapeutic properties. The poly I·poly C degradation curve was monospecific and simply leads to small, non-bioactive, residual nucleic acid material. Whereas, in contrast, the degradation curve of mismatched dsRNA was biphasic: in the first phase, Phase 1, of the degradation curve, smaller, bioactive fragments were formed; yet the parent input molecule was approximately 1,000 base pairs long corresponding to a sedimentation (analytical ultracentrifugation) value $(S_{20,w})$ of about 11.0–15.0 S, the daughter (partial hydrolysis) products were only 50–100 base pairs long. Surprisingly, I found that they expressed, still, high bioactivity as intracellular catalysts of component parts of the critical 2'-5'A natural defense pathway of man. These fragments were not detectably present when I sampled the vials of poly I·C which had been exposed to comparable amounts of dsRNA degradative enzymes such as $S_1$ nuclease under similar conditions.

In Phase 2 of my mismatched dsRNA degradation curve, fragments of dsRNA less than 50 base pairs were recovered. I term these latter fragments the "nuclease resistant core" and I was unable to distinguish such residual fragments from those generated with poly I·poly C. Accordingly, I conclude that during the biodegradation of certain configurations of dsRNA (namely, mismatched dsRNA) that particular classes of biofragments of dsRNA are created and that such fragments convey special and unexpected properties such as the ability to effectively penetrate special bodily fluids (compartments) outside the systemic circulation, or blood supply. These compartments include, but are not limited to, various serosal and/or mucousal surfaces such as synovial lining, urethral surface, cervical lining as well as cerebral spinal, and ocular fluid compartments.

EXAMPLE 3

Experiments were then conducted in vitro/in vivo to validate the assumption that novel molecular species of dsRNA, generated during the biodegradation process, contributed to the unexpectedly high level of mediators of the natural defense system (e.g., 2'-5'A system) in various biological (bodily) fluids.

A. Nuclease Degradation of Poly I·Poly C Versus Mismatched dsRNAs

The susceptibility of double-stranded RNAs (dsRNAs) to hydrolysis by nucleases was studied utilizing radioactive poly I·poly C and mismatched dsRNA. [8-$^{14}$C] polyinosinic acid (sp. act. 3.6 µCi/µmole) was purchased from P-L Brochemicals. This labeled poly I was >1000 bases in length. The [8-14C] poly I was mixed with unlabeled poly I·poly C or mismatched dsRNA and the mixtures were heat denatured and reannealed to yield radioactive dsRNAs.

Initial studies measured digestion by $S_1$ nuclease (E.C.3.1.30.1). $S_1$ nuclease will digest single-stranded nucleic acids, leaving double-stranded regions intact. Digestion of poly I·poly C by $S_1$ nuclease yielded monophasic kinetics with a rate of 1.4% of the dsRNA rendered TCA soluble per minute. After heat denaturation, the hydrolysis rate rose to 1.8% per minute.

Similar experiments utilizing labeled mismatched dsRNA demonstrated that the kinetics of digestion were biphasic. Native mismatched dsRNA had an initial fast component of digestion (3.2% per minute) followed by a much slower component of digestion (0.5% per run). Denatured mismatched dsRNA showed relatively rapid degradation (4.5% per minute).

The total degradation for native poly I·poly C and mismatched dsRNA over the 45 minute time course of these experiments was similar. As previously reported (Carter et al, *J. Mol. Biol.*, 70:567, 1972), the rate of hydrolysis of mismatched dsRNA was initially greater than that for poly I·poly C. However, the biphasic kinetics of mismatched dsRNA degradation demonstrates an apparent physical difference between this material and well-registered (fully base-paired) poly I·poly C molecules. These results suggest a significant difference in secondary or tertiary structure yielding differences in nuclease susceptibility between these dsRNAs and unexpected biological results, the results of which are reported in this patent application. In addition, the significant 6-fold decrease in rate of hydrolysis between the biphasic components of certain dsRNA and the relatively low hydrolysis of the slow component indicate the existence of a relatively nuclease resistant core in this class of dsRNA which is not apparent in poly I·poly C.

Nuclease degradation of mismatched dsRNA was also carried out using a standard tissue culture medium (RPMI 1640) supplemented with 10% heat inactivated fetal calf serum or human serum. This serum is a source of ribonucleases. Degradation of mismatched dsRNA with the medium was rapid, with approximately 40% of this dsRNA rendered TCA soluble within 3 minutes. Further digestion, for up to two hours did not yield a significant amount of additional degradation. Serial dilution of the media followed by a 3 minute incubation in the presence of mismatched dsRNA again demonstrated an approximate 50% degradation at a 1/16 dilution which was not further enhanced by more concentrated serum. Since the amount of TCA precipitable material stays relatively constant over long time periods and a significant range of dilutions, the prolonged stability of the TCA precipitable material is probably not due to the preferential degradation of TCA soluble material. These results again suggest the presence of a nuclease resistant core within the mismatched dsRNA molecule.

B. Molecular Weight of the Nuclease Resistant Core of Mismatched dsRNA

Molecular weight was assayed by the determination of sedimentation coefficients. Untreated dsRNA samples were run in a Beckman Model E ultracentrifuge at 48,000 RPM, 20° C. Five points at 8 minute intervals were used to calculate the sedimentation coefficients. dsRNA samples were diluted to an $OD_{260}$ of 0.63 in buffer A (0.15M NaCl, 0.01M sodium phosphate, 0.001M $MgCl_2$, pH 7.2). The $S_1$ nuclease treated dsRNA samples were run at 52,000 RPM[1] 20° C. in buffer A at an $OD_{260}$ of 0.65. Sedimentation coefficients. Sedimentation coefficients were calculated by the half-height and second moment methods.

The sedimentation coefficients of the dsRNA as determined by half-height and second moment methods were 12.74 and 13.29, respectively. Following hydrolysis with $S_1$ nuclease, the sedimentation coefficients of the dsRNA as determined by the half-height method decreased to 6.18 and as determined by the second moment method decreased to 7.21. These data show that treatment with $S_1$ nuclease degrades the mismatched double-stranded RNA to low molecular weight fragments.

C. Biological Activity of the Nuclease Resistant Core of dsRNA

The biological activity of the $S_1$ nuclease-digested dsRNA was tested in a standard tissue culture tumor growth inhibition assay. dsRNA was incubated with $S_1$ nuclease for up to 120 minutes and then used to inhibit the growth of the human fibrosarcoma cell line, HT1080 C14. The percentage of untreated control cell growth seen after 72 hours of treatment with 50 µg/ml of the $S_1$ nucelase-digested mismatched dsRNA. Untreated dsRNA inhibited cell growth approximately 50%. Similar inhibition was seen with the $S_1$ nuclease treated mismatched dsRNA regardless of the extent of the $S_1$ nuclease treatment. Heat denaturation combined with $S_1$ nuclease treatment abolished the antiproliferative effect of the mismatched dsRNA.

These results indicate that the antiproliferative activity of mismatched dsRNA is maintained even after prolonged nuclease treatment. Since the nuclease resistant core appears to be generated within the first 15-20 minutes of digestion in this system, the growth inhibition at later time points suggests that the antiproliferative activity of dsRNA resides in the nucelase resistant core and this, in turn, may account for the surprising high yields of biologically active mediators in various bodily compartments.

In order to further explore the biological activity of the nuclease resistant core, dsRNA was digested for 60 minutes with $S_1$ nuclease. An aliquot of this material was then ethanol precipitated to potentially remove small degradation products which do not precipitate by this procedure. As a measure of biological activity, the human glioma cell line A1235 was treated with 200 µg/ml of native dsRNA, $S_1$ nuclease digested Ampligen and ethanol precipitated, digested dsRNA. After 72 hours in culture, the A1235 cells were inhibited 99.8% by the Ampligen, 78.4% by the $S_1$, nuclease treated Ampligen and 84.4% by the ethanol precipitated, $S_1$ nuclease treated Ampligen. Thus, the antiproliferative activity of dsRNA was maintained throughout these different treatments.

The ability of these preparations to induce 2-5 A synthetase [ATP:(2',5'-oligo(A)adenylyl-transferase (EC 2.7.7.19)] in these A1235 cells was also measured. Cell pellets were washed with PBS, resuspended in 5 ml of lysing buffer (20 mM Tris, pH 7.5, 0.1 mM EDTA, 0.25M sucrose. 50 mM KCl, 2 mM $MgCl_2$ and 1 mM DTT) and kept on ice for 5 minutes. After washing twice with PBS, the cell pellets were resuspended in 0.1 ml buffer B (20 mM HEPES, pH 7.5, 5 mM $MgCl_2$, 120 mM DTT, and 10% glycerol) containing 0.5% Nonidet-P40 and kept on ice 10 minutes to lyse the cells. Cytoplasmic extracts were obtained by centrifugation for 6 minutes at 8000 g and stored in 50 µL aliquots at −70° C. 2-5A synthetase was assayed as described (Suhadolnik et al, Biochemistry 22:4153, 1983). Thawed cell extract (equivalent to 25 µg protein) was mixed with 30 µL packed poly(rI)·poly(rC)-agarose and incubated at 25° C. for 20 minutes. Unbound protein was removed by two washes with 0.4 mL buffer B. Enzymatic synthesis of 2'-5'-oligoadenylates (2-5A) was initiated by the addition of 10 µL of buffer B containing 2.5 mM [$^{32}$P]ATP (0.12 Ci/mmole), 2.5 mM DTT, 3 units/mL creatine phosphokinase, and 10 mM creatine phosphate. After 20 hour incubation at 30° C., the agarose was pelleted by centrifugation (3 minutes, 8000 g, 25° C.). The mixture of 2-5A in the supernatatn was analyzed by DEAE-cellulose column chromatography as described by Doetsch et al. (Nature, 291:355, 1981). Product formation was determined by the amount of radioactivity displaced from the DEAE-cellulosse columns with 0.35M KCl buffer divided by the total radioactivity recovered.

The synthesis of 2-5A in enzyme incubation with cell-free extracts of dsRNA nuclease-treated dsRNA, and the nuclease-treated dsRNA following precipitation show the effect of time on the conversion of ATP to 2-5A. There are several striking results. First, following 18 hour incubations of the cell-free extracts with untreated mismatched dsRNA, the specific activity of the 2-5A synthetase was 41.5. Second, following $S_1$ nuclease treatment, there is a marked increase in the conversion of ATP to 2-5A. For example, after an 18 hour incubation, the specific activity is 284, which is about 7 times greater than that observed with the untreated mismatched dsRNA. Third, the dsRNA treated with $S_1$ nuclease, following precipitation, showed a maximum synthesis of 2-5A after 12 hour incubation. These data show that the enzymatic synthesis of the trimer, tetramer and higher oligomers of 2-5A is significantly increased following $S_1$ nuclease treatment of mismatched dsRNA. The positive association between the increase in enzyme activity with the decreased size of the dsRNA is evidence that there may be interaction with the allosteric modifier, i.e., the partially degraded mismatched dsRNA, such that it can bind to and activate the 2-5A synthetase much better than the unntreated mismatched dsRNA. The therapeutic implication of these findings are obvious. By contrast, when low molecular weight degradation products of nuclease $S_1$ treated mismatched dsRNA were removed by precipitation, there was a maximal synthesis of 2-5A following 12 hour incubation. This maximal 2-5A synthetase activity of the $S_1$ nuclease digested dsRNA following precipitation suggests that the nuclease resistant core can activate the 2-5A synthetase in a manner equivalent to the activation by $S_1$ nuclease-treated mismatched dsRNA after 18 hour incubations.

These data confirm the presence of biologically active fragments of mismatched dsRNA and explains a physical basis for the therapeutic activity of these fragments in the biological fluid. These data also demonstrate that the biologically active fragments are more active than the parent compound.

EXAMPLE

Figure 3:
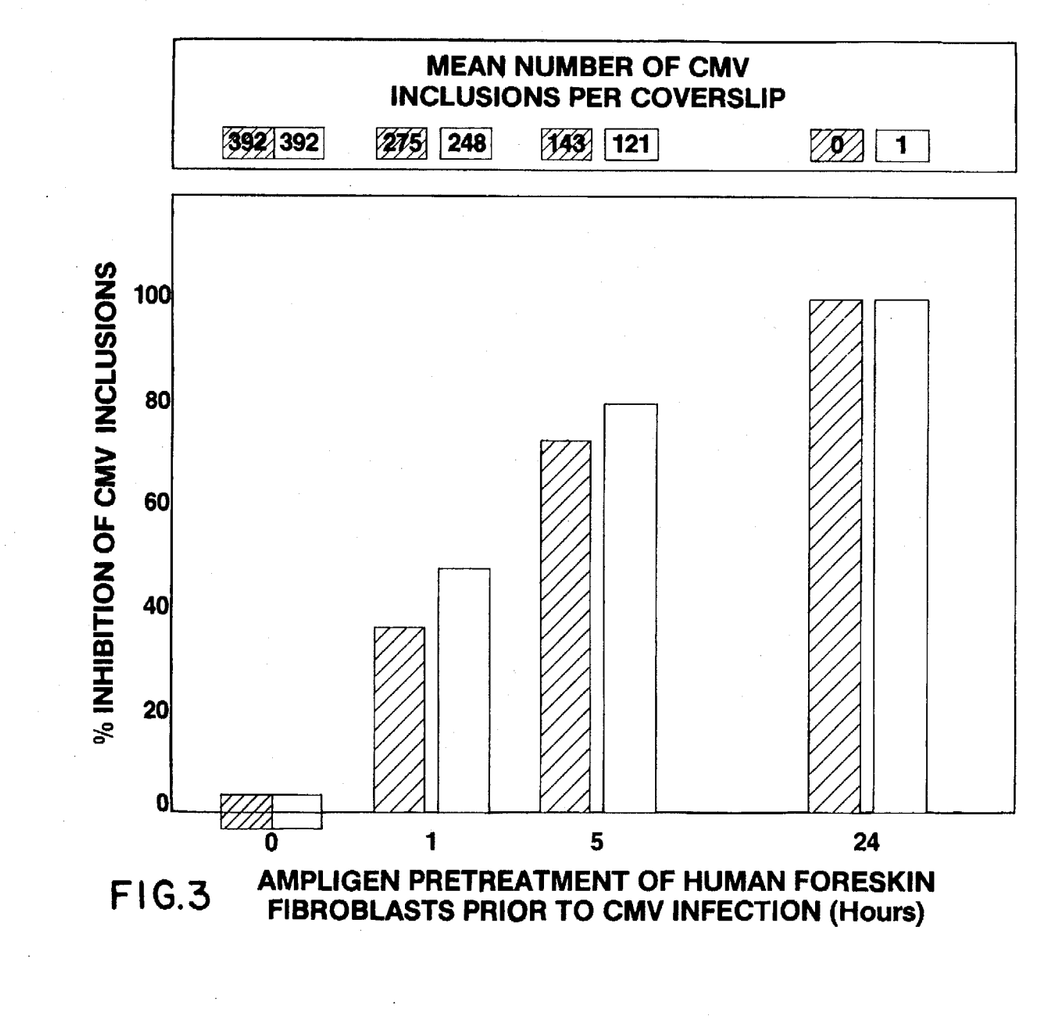
FIG. 3 is a graph showing the effect of dsRNA inhibition on cytomegalovirus infection of cells pretreated with a dsRNA as compared with untreated cells as described in Example 4.

Another illustration of how the invention can be practiced is by preventing sexual transmitted disease such as cytomegalovirus or CMV (see N.Y. Times, Jul. 14, 1988, page B6, which summarizes the sharp rise in sexual related disease). Cytomegalovirus (a member of the herpes virus family) affects more than 1 million in the United States alone and people with impaired immune systems may develop gastrointestinal problems or blindness (both serous surfaces which became viral infected and compartments not readily transversed by many systemically applied antiviral agents). CMV is sexually transmitted. By generating bioactive fragments over time, such as one does by administering mismatched dsRNA (Ampligen) one achieves a much higher level of inhibition. For example, FIG. 3 shows a 100% inhibition of CMV when exposed to Ampligen fragments for 24 hours. Such controlled release of bioactive material cannot be readily achieved by topical salves etc., when using dsRNAs of a relatively non-toxic variety.

The generation of bioactive fragments of dsRNA over time was illustrated in tissue culture studies conducted with cytomegalovirus, sometimes called cytomegalic inclusion disease which refers to the intranuclear inclusions found in enlarged cells infected with the virus. Human cytomegaloviruses are a subgroup of viral agents closely related to or members of the herpes group of viruses. Although ubiquitous, incidence of sexually transmitted CMV has recently been reported with estimates of over one million persons infected in the United States in 1988. The infection is usually asymptomatic, but people with impaired immune systems may develop gastrointestinal problems or blindness. Newborns are particularly susceptible and CMV may cause abortion, stillbirth or post natal death. The Merck Manual, 14th Edition (1982), pp. 205–206, gives no specific therapy for the disease.

In this experiment, the following procedures and materials were used.

Human Foreskin Fibroblasts (HFF) were isolated from newborns and maintained at low passage (<20) in Minimum Essential Medium with Earle's salts supplemented with 10% fetal bovine serum, 2 mM L-glutamine, 1 mM sodium pyruvate, 20 mM HEPES buffer, and antibiotics. Once cells reached confluency, they were maintained as above with the exception of 5% fetal bovine serum. Weekly assays of cells were negative for bacterial and mycoplasmal contamination.

A stock preparation of human Cytomegalovirus (CMV, ATCC #VR-538, strain AD169) was used throughout the study. It consisted of a second passage through HFF that was harvested when CMV cytopathic effect involved 75% of the host cells. Cell-free stock virus was dispensed into storage tubes and maintained at −120° C. Bacterial and mycoplasmal sterility tests were negative. The infectious titer of the CMV stock preparation was determined on HFF cells and was $4 \times 10^6$ fluorescent forming inclusions/ml (see below).

Lyophilized, clinical grade Ampligen® (mismatched dsRNA; poly I·poly $C_{12}$,U, Hem Research, Inc., Rockville, Md., USA) was used. Using the manufacturer's directions, the Ampligen was reconstituted, aliquoted and stored at $-120°$ C. For each experiment, a fresh aliquot was thawed with swirling in a $50°$ C. water bath and diluted in the above described tissue culture medium at desired concentrations.

The drug was incubated with HFF cells under various conditions. These variations included: (1) concentration of Ampligen; (2) sequence of Ampligen exposure relative to virus uptake; and (3) length of time that HFF were exposed to Ampligen. Viability of Ampligen-treated HFF was identical to untreated HFF as determined by trypan blue exclusion (i.e., >99%).

Confluent HFF were cultivated on circular coverslips in one dram (capacity 3.7 ml) shell vials. Viral infection was initiated by incubating the shell vials with 0.25 ml of an appropriate diultion of CMV. The HFF were exposed to the CMV at $37°$ C. for one hour at 700×g to allow for virus uptake. The vials were washed two to three times to remove extracellular virus. The vials were refed with one ml of tissue culture medium and normally were incubated for 18 to 24 hours at $37°$ C. for 72 hours.

CMV replication was quantified as follows. Viral replication was halted by fixing the HFF in 100% acetone. The coverslips containing the adherent HFF were rinsed and incubated with an anti-CMV mouse monoclonal antibody (DuPont) specific for the 72 kilodalton immediate early protein. Bound antibody was detected by the addition of an FITC-labeled antimouse IgG F $(ab)_2$ (SIGMA). Viral infected cells exhibited bright apple-green nuclear fluorescence when viewed at 250×magnification with an epifluorescent microscope. The number of CMV infected cells (i.e., those exhibiting fluorescent nuclear inclusions) were counted in the microscope. The positive stock preparation was diluted so that, in the absence of Ampligen, it produced between 200 and 1200 CMV-infected cells per coverslip after 24 hours of incubation. This was achieved with a multiplicity of infection (MOI) of 0.04.

The mean number of CMV inclusions from replicate coverslips for each experimental condition was determined and compared to that of a positive control which did not receive Ampligen. Negative controls which were not exposed to either Ampligen or CMV were evaluated in parallel. The antiviral activity of Ampligen was expressed according to the formula:

$$\{\% \text{ inhibition of } CMV \text{ Inclusions} = 100\% - \left[\left(\frac{\text{Mean \# of } CMV \text{ Inclusions/Coverslip in Ampligen Treated } HFF}{\text{Mean \# of } CMV \text{ Inclusions/Coverslip in Untreated Control } HFF}\right)\right]$$

Effect of the length of Ampligen pretreatment on the infection of Human Foreskin Fibroblasts with Cytomegalovirus is given in FIG. 3. Replicate monolayers of human foreskin fibroblasts were either: (1) pretreated with 10 µg/ml Ampligen (open bars) or (2) pretreated with 100 µg/ml (cross-hatched bars) for the indicated time intervals prior to CMV uptake. The extent of CMV infection was determined 24 hours post viral uptake by the described IFA method. The mean number of CMV inclusions per coverslip for Ampligen-treated cultures was compared to that of drug-free controls. The results indicate that the length of Ampligen pretreatment is directly proportional to the extent of inhibition of CMV infection. Maximal CMV inhibition is achieved when HFF are pretreated with Ampligen for 24 hours.

This study demonstrates the ability of mismatched dsRNA to exert an antiviral effect against CMV that increases over time and CMV-sensitivity to the mismatched dsRNA, after time, irrespective of the concentration used, a sustained release level not achieved by topical applications of dsRNAs of a relatively non-toxic variety.

What is claimed is:

1. A method of treating a herpes virus infection comprising parenterally administering to a patient in need of same an effective amount of a mismatched dsRNA $rI_n \cdot r(C_{12},U)_n$ wherein n is from 4 to 29.

2. The method of claim 1 wherein the mismatched dsRNA is administered to provide a level of from 0.1 to 1,000 micrograms of dsRNA per milliliter of the patient's body fluid.

* * * * *